United States Patent [19]

Hudson et al.

[11] Patent Number: 5,145,962
[45] Date of Patent: Sep. 8, 1992

[54] HUMAN PRO RELAXIN POLYPEPTIDES

[75] Inventors: Peter J. Hudson, Bulleen; John Shine, Swinger Hill; Hugh D. Niall, Elwood; Geoffrey W. Tregear, Hawthorn, all of Australia

[73] Assignee: Howard Florey Institute of Experimental Physiology and Medicine, Melbourne, Australia

[21] Appl. No.: 681,828

[22] Filed: Apr. 8, 1991

Related U.S. Application Data

[60] Division of Ser. No. 549,668, Jul. 6, 1990, Pat. No. 5,053,488, which is a continuation of Ser. No. 21,878, Mar. 4, 1987, abandoned, which is a division of Ser. No. 863,819, May 12, 1986, Pat. No. 4,758,516, which is a continuation of Ser. No. 522,956, Aug. 12, 1983, abandoned.

[30] Foreign Application Priority Data

Aug. 12, 1982 [AU] Australia ............................. 5352/82

[51] Int. Cl.⁵ ............................................. C07K 7/10
[52] U.S. Cl. ................................... 530/324; 530/303; 530/851; 530/853; 530/350; 435/69.4
[58] Field of Search ............... 530/303, 374, 350, 851, 530/853; 435/69.4

[56] References Cited

U.S. PATENT DOCUMENTS 5,053,488 10/1991 Hudson et al. ..................... 530/324

Primary Examiner—David L. Lacey
Assistant Examiner—Nina Ossanna
Attorney, Agent, or Firm—Sughrue, Mion, Zinn, Macpeak & Seas

[57] ABSTRACT

Genes and DNA transfer vector for the expression of human preprorelaxin; subunits thereof, including genes and transfer vectors for expression of human prorelaxin and the individual A, B and C peptide chains thereof; and equivalents of all such genes. Methods for synthesis of the peptides involving recombinant DNA techniques.

10 Claims, 8 Drawing Sheets

|—Signal Peptide—→

```
                      -20
Met Pro Arg Leu Phe Leu Phe His Leu Leu Glu Phe Cys Leu Leu
AUG CCU CGC CUG UUC UUG UUC CAC CUG CUA GAA UUC UGU UUA CUA 10                                        20
Val Ile Lys Leu Cys Gly Arg Glu Leu Val Arg Ala Gln Ile Ala
GUU AUU AAA UUA UGC GGC CGC GAA UUA GUU CGC GCG CAG AUU GCC 40                                        30
Asp Ala Pro Gln Thr Pro Arg Pro Val Ala Glu Ile Val Pro Ser
GAU GCU CCU CAG ACA CCU AGA CCA GUG GCA GAA AUU GUA CCA UCC 70                                        80
Ile Ala Asn Leu Pro Pro Glu Leu Lys Ala Ala Leu Ser Glu Arg
AUU GCU AAU UUG CCA CCG GAG CUG AAG GCA GCC CUA UCU GAG AGG 100                                       110
Asp Ser Asn Leu Ser Phe Glu Glu Phe Lys Lys Leu Ile Arg Asn
GAU UCC AAU CUU AGC UUU GAA GAA UUU AAG AAA CUU AUU CGC AAU

┌—A-chain—→
         130                              140
Leu Gly Leu Asp Thr His Ser Gln Lys Lys Arg Arg Pro Tyr Val
UUA GGC UUG GAU ACU CAU UCU CAA AAA AAG AGA CGA CCC UAC GUG 160
Leu Ala Lys Tyr Cys ***
CUU GCU AAA UAU UGC UGA
```

*FIG. 2A.*

```
                                                      ┌─B-chain─→
 -10                                          -1 │ 1
 Leu Asn Gln Phe Ser Arg Ala Val Ala Ala  Lys Trp Lys Asp Asp
 CUG AAC CAA UUU UCC AGA GCA GUC GCG GCC  AAA UGG AAG GAC GAU ┌─C-peptide─→
                                      30             │
 Ile Cys Gly Met Ser Thr Trp Ser Lys Arg Ser Leu  Ser Gln Glu
 AUU UGC GGC AUG AGC ACC UGG AGC AAA AGG UCU CUG  AGC CAG GAA 60
 Phe Ile Asn Lys Asp Thr Glu Thr Ile Ile Ile Met Leu Glu Phe
 UUC AUC AAC AAA GAU ACA GAA ACU AUA AUU AUC AUG UUG GAA UUC 90
 Gln Pro Ser Leu Pro Glu Leu Gln Gln Tyr Val Pro Ala Leu Lys
 CAA CCA UCA UUA CCA GAG CUA CAG CAG UAU GUA CCU GCA UUA AAG 120
 Arg Gln Ser Glu Ala Ala Asp Ser Asn Pro Ser Glu Leu Lys Tyr
 AGG CAA AGU GAA GCC GCA GAC AGC AAU CCU UCA GAA UUA AAA UAC 150
 Ala Leu Phe Glu Lys Cys Cys Leu Ile Gly Cys Thr Lys Arg Ser
 GCA CUG UUU GAG AAA UGU UGC CUA AUU GGU UGU ACC AAA AGG UCU
```

```
                                                                    B-chain
          -10                                               -1  │ 1
     Leu  Leu  Asn │Gln│ Phe  Ser │Arg│ Ala  Val  Ala  Ala │Lys  Trp
     CUA  CUG  AAC │CAA│ UUU  UCC │AGA│ GCA  GUC  GCG  GCC │AAA  UGG
     **   ***  * * │***│ **   **  │***│ *    **   *    **  │*    *
     CUC  CUG  AGC │CAA│ CUU  CCC │AGA│ GAA  AUC  CCA  GGC │CAG  AGU
     Leu  Leu  Ser │Gln│ Leu  Pro │Arg│ Glu  Ile  Pro  Gly │Gln  Ser
                                                            -1  │ 1

20
     Ala  Gln  Ile  Ala │Ile  Cys  Gly│ Met  Ser  Thr │Trp│ Ser  Lys
     GCG  CAG  AUU  GCC │AUU  UGC  GGC│ AUG  AGC  ACC │UGG│ AGC  AAA
     *    *    *    *   │**   **   ***│ *    **   *   │***│ *    * *
     CUG  UGG  GUG  GAG │AUC  UGU  GGC│ UCC  GUC  UCC │UGG│ GGA  AGA
     Leu  Trp  Val  Glu │Ile  Cys  Gly│ Ser  Val  Ser │Trp│ Gly  Arg

┌─45──
     Val  │Ala  G
     GUG  │GCA  G gtgagagctcccgccccctccggcctccc — — — — — — — — 
     *    │***  *
     CCG  │GCA  G
     Pro  │Ala  G 50
           lu  Ile  Val │Pro  Ser│ Phe │Ile│ Asn │Lys  Asp│ Thr
     aacttaacag AA  AUU  GUA │CCA  UCC│ UUC │AUC│ AAC │AAA  GAU│ ACA
           **  *    *   │***  ***│ * * │***│ * * │***  ***│ **
           AA  ACC  AUG │CCA  UCC│ UCC │AUC│ ACC │AAA  GAU│ GCA
           lu  Thr  Met │Pro  Ser│ Ser │Ile│ Thr │Lys  Asp│ Ala
                                    50
```

```
        60                                                          70
┌───┐┌───────────────────┐┌───────────────────────┐┌───────┐┌────────────────┐
│Glu││Thr  Ile  Ile  Ile ││Met  Leu  Glu  Phe     ││Ile Ala││Asn  Leu  Pro   │
│GAA││ACU  AUA  AUU  AUC ││AUG .UUG  GAA  UUC     ││AUU GCU││AAU  UUG  CCA   │
│***││ *   **   *   **   ││***  ***  ***  **      ││ **  **││***  ***  ***   │
│GAA││AUC  UUA  AAG  AUG ││AUG  UUG  GAA  UUU     ││GUU CCU││AAU  UUG  CCA   │
│Glu││Ile  Leu  Lys  Met ││Met  Leu  Glu  Phe     ││Val Pro││Asn  Leu  Pro   │
└───┘└───────────────────┘└───────────────────────┘└───────┘└────────────────┘

90
┌───┐┌───┐┌────────────────────┐┌──────────┐┌───┐┌────────────────┐
│Leu││Pro││Glu  Leu  Gln  Gln  ││Tyr Val Pro│ Ala││Leu││Lys  Asp  Ser│
│UUA││CCA││GAG  CUA  CAG  CAG  ││UAU GUA CCU│ GCA││UUA││AAG  GAU  UCC│
│ * ││ * ││***  ***  **   **   ││           │ ***││ * *││***  ***  **│
│CUG││AGA││GAG  CUA  CAA  CAA  ││           │UCU GCA│UCA│AAG  GAU  UCG│
│Leu││Arg││Glu  Leu  Gln  Gln  ││           │Ser Ala│Ser│Lys  Asp  Ser│
└───┘└───┘└────────────────────┘└──────────┘└───┘└────────────────┘

120
┌───────┐┌───┐┌───────────┐┌───────┐┌───┐┌───────────────┐┌────────────────┐
│Arg Gln││Ser││Glu  Ala   ││Ala Asp││Ser││Ser Asn Pro Ser││Glu  Leu  Lys   │
│AGG CAA││AGU││GAA  GCC   ││GCA GAC││AGC││AGC AAU CCU UCA││GAA  UUA  AAA   │
│ **  ***││ * *││***  **   ││ * *│***│ * │ *   *  ** *  * │***  ***  ***   │
│AGA CAA││AAU││GAA  GCA   ││GAA GAC││AAA││AAA AGU CUU UUA││GAA  UUA  AAA   │
│Arg Gln││Asn││Glu  Ala   ││Glu Asp││Lys││Lys Ser Leu Leu││Glu  Leu  Lys   │
└───────┘└───┘└───────────┘└───────┘└───┘└───────────────┘└────────────────┘

140                                          150
             ┌─────────────────┐┌───┐┌─────┐┌────────────────┐┌───────┐┌────────┐
│Pro Tyr Val Ala│Leu││Phe││Glu  Lys  Cys  Cys││Leu Ile││Gly  Cys│
│CCC UAC GUG GCA│CUG││UUU││GAG  AAA  UGU  UGC││CUA AUU││GGU  UGU│
│ *       **  **│***││   ││***  ***  ***  ** ││ *   * ││***  ***│
│UUC CGU AUG ACA│CUG││AGC││GAG  AAA  UGU  UGU││CAA GUA││GGU  UGU│
│Phe Arg Met Thr│Leu││Ser││Glu  Lys  Cys  Gys││Gln Val││Gly  Cys│
        └──────→
         A-chain
```

*FIG. 3C.*

|     | Pro | Glu | Leu | Lys | Ala | Ala | Leu | Ser | Glu | Arg | Gln | Pro | Ser |
|-----|-----|-----|-----|-----|-----|-----|-----|-----|-----|-----|-----|-----|-----|
|     | CCG | GAG | CUG | AAG | GCA | GCC | CUA | UCU | GAG | AGG | CAA | CCA | UCA |
|     | * * | *** | *** | *** | *** | *   | *   | *** | *** | *** | *** | *** | *** |
|     | CAG | GAG | CUG | AAG | GCA | ACA | UUG | UCU | GAG | AGG | CAA | CCA | UCA |
|     | Gln | Glu | Leu | Lys | Ala | Thr | Leu | Ser | Glu | Arg | Gln | Pro | Ser |

80

|     | Asn | Leu | Ser | Phe | Glu | Glu | Phe | Lys | Lys | Leu | Ile | Arg | Asn |
|-----|-----|-----|-----|-----|-----|-----|-----|-----|-----|-----|-----|-----|-----|
|     | AAU | CUU | AGC | UUU | GAA | GAA | UUU | AAG | AAA | CUU | AUU | CGC | AAU |
|     | *** | *** | * * | *** | *** | *** | *** | *** | *** | **  | *** | *   | **  |
|     | AAU | CUU | AAC | UUU | GAA | GAA | UUU | AAG | AAA | AUU | AUU | CUU | AAC |
|     | Asn | Leu | Asn | Phe | Glu | Glu | Phe | Lys | Lys | Ile | Ile | Leu | Asn |

100

A-chain →

|     | Tyr | Leu | Gly | Leu | Asp | Thr | His | Ser | Gln | Lys | Lys | Arg | Arg |
|-----|-----|-----|-----|-----|-----|-----|-----|-----|-----|-----|-----|-----|-----|
|     | UAC | UUA | GGC | UUG | GAU | ACU | CAU | UCU | CAA | AAA | AAG | AGA | CGA |
|     | **  | *** | **  | **  | *** | *   | *** | **  | *   | *** | *** | *** | *   |
|     | AAC | UUA | GGU | UUA | GAU | AAA | CAU | UCC | AGA | AAA | AAG | AGA | CUG |
|     | Asn | Leu | Gly | Leu | Asp | Lys | His | Ser | Arg | Lys | Lys | Arg | Leu |

130

|     | Thr | Lys | Arg | Ser | Leu | Ala | Lys | Tyr | Cys | *** |
|-----|-----|-----|-----|-----|-----|-----|-----|-----|-----|-----|
|     | ACC | AAA | AGG | UCU | CUU | GCU | AAA | UAU | UGC | UGA |
|     | *   | *   | *   |     | *   | *** | * * |     | *** | *** |
|     | AUC | AGA | AAA | GAU | AUU | GCU | AGA | UUA | UGC | UGA |
|     | Ile | Arg | Lys | Asp | Ile | Ala | Arg | Leu | Cys | *** |

HUMAN PRO RELAXIN POLYPEPTIDES

The invention described herein was made in the course of work under a grant or award from the Department of Health and Human Services.

This a divisional of application Ser. No. 07/549,668, filed Jul. 6, 1990, now U.S. Pat. No. 5,053,488, which is a continuation of application Ser. No. 07/021,878, filed Mar. 4, 1987, now abandoned, which is a divisional of application Ser. No. 06/863,819, filed May 12, 1986, now U.S. Pat. No. 4,758,516, which is a continuation of application Ser. No. 06/522,956, filed Aug. 12, 1983, now abandoned.

This invention relates to the molecular cloning and characterization of the gene sequence coding for human relaxin. The invention is also concerned with recombinant DNA techniques for the preparation of human relaxin, prorelaxin and preprorelaxin.

More specifically, this invention relates to an isolated and purified ("cloned") human gene coding for prorelaxin, preprorelaxin, and the A and/or B and/or C peptide chains of human relaxin, methods for isolating and purifying the genes and methods for transferring the genes to and replicating the genes in a host cell. The cloned genes are expressed by the host cell when fused with a host-expressable prokaryotic or eukaryotic gene. The genes are thus useful in the production of human relaxin for therapeutic purposes.

The invention also relates to the peptides human relaxin, prorelaxin and preprorelaxin, to the individual peptide chains which comprise these sequences and to modified forms of these peptides.

The invention further relates to modified genes coding for the individual relaxin chains and for the above-mentioned modified forms.

Note: References referred to by number used in the following description are collected at the end of the description.

Pioneering work by Hisaw (1) suggested an important role for the peptide hormone relaxin in mammals through its effects in dilating the pubic symphysis, thus facilitating the birth process. Relaxin is synthesized and stored in the corpora lutea of ovaries during pregnancy and is released into the blood stream prior to parturition. The availability of ovaries has enabled the isolation and amino acid sequence determination of relaxin from pig (2,3) rat (4) and shark (5). The biologically active hormone consists of two peptide chains (known as the A and B chains) held together by disulphide bonds, two inter-chain and one intra-chain. The structure thus closely resembles insulin in the disposition of disulphide bonds which has led to speculation of a common ancestral gene for these hormones (2,3).

Recombinant DNA techniques have been applied to the isolation of cDNA clones for both rat and porcine relaxins (6), see also Australian Patent Application No. 11834/83 (PF 2696/82). Synthetic undecamer nucleotides, prepared on the basis of amino acid sequence information, were used as primers for the synthesis of cDNA probes greatly enriched in relaxin cDNA sequences which identified relaxin cDNA clones in libraries derived from ovarian tissue. The relaxin structural gene was found to code for a single chain precursor which resembles preproinsulin in the overall configuration, i.e., signal peptide/B chain/C peptide/A chain.

Pig and rat preprorelaxins contain an unexpectedly large connecting peptide of 105 and 104 residues respectively in comparison to rat insulin with a C peptide of about 30 residues. A high degree of sequence homology in the C-peptide of rat and pig relaxin suggests a role beyond simply ensuring the correct disulphide bond formation of the A and B chains. We predicted that structural constraints on sequence divergence applying during evolution would have resulted in the C-peptide region having a similarly high degree of sequence homology in the human relaxin gene. Accordingly, as described hereinafter, we have used probes based on the C-peptide region of porcine rather than rat relaxin in the selection of the human relaxin gene because the accumulation of protein sequence data indicated that human proteins are in general less divergent from porcine than from rat proteins (8).

Although it has been the long term goal of several groups to determine the structure of human relaxin and so establish a route to clinical intervention in cases of difficult labour, the limited availability of human ovaries during pregnancy has prevented direct amino acid sequence determination. Our approach was to screen directly for the human relaxin gene in a genomic library using a region of the porcine relaxin cDNA as a probe. This approach resulted in the successful identification of genomic clone from which the structure of the entire coding region of preprorelaxin has been determined.

It is now believed that either or both the presently-described gene which we have designate "H1" and the "H2" gene described in our issued U.S. Pat. No. 4,738,516 are expressed in human reproductive tissue, for example ovary and placenta, and/or other tissues including but not limited to gut, brain and skin, since both genes express peptides with relaxin-like activity.

The corpora lutea of the ovary as well as decidual and placental tissues are the most likely sites for expression of relaxin-related genes. However, in view of the wide distribution of many peptide hormones it is highly likely that the relaxin gene is also expressed in non-reproductive tissues, including brain and the gastrointestinal tract. Relaxin has the general properties of a growth factor and is capable of altering the nature of connective tissue and influencing smooth muscle contraction. We believe that one or both of the gene structures described in this and the copending patent application PF 7247/82 to be widely distributed in the body. We suggest that the relaxin peptides expressed from these genes will play an important physiological role in addition to their well documented hormonal function during reproduction.

The following abbreviations are used in this description.

H1 - the relaxin gene described herein, being deduced from a genomic clone.

H2 - the relaxin gene described in copending Application No. PF 7247/82, being deduced from a cDNA clone.

| DNA - deoxyribonucleic acid | A - Adenine |
|---|---|
| RNA - ribonucleic acid | T - Thymine |
| cDNA - complementary DNA (enzymatically synthesized from an mRNA sequence) | G - Guanine |
| | C - Cytosine |
| | U - Uracil |
| mRNA - messenger RNA | |

The coding relationships between nucleotide sequence in DNA and amino acid sequence in protein are collectively known as the genetic code, which is set out below.

| First position (5' end) | Second position | | | | Third position (3' end) |
|---|---|---|---|---|---|
| | U | C | A | G | |
| U | Phe | Ser | Tyr | Cys | U |
| | Phe | Ser | Tyr | Cys | C |
| | Leu | Ser | Stop | Stop | A |
| | Leu | Ser | Stop | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

The abbreviations used for the amino acids in the table are identified as follows.

| | | | |
|---|---|---|---|
| Phenylalanine | (Phe) | Histidine | (His) |
| Leucine | (Leu) | Glutamine | (Gln) |
| Isoleucine | (Ile) | Asparagine | (Asn) |
| Methionine | (Met) | Lysine | (Lys) |
| Valine | (Val) | Aspartic acid | (Asp) |
| Serine | (Ser) | Glutamic acid | (Glu) |
| Proline | (Pro) | Cysteine | (Cys) |
| Threonine | (Thr) | Tryptophan | (Try) |
| Alanine | (Ala) | Arginine | (Arg) |
| Tyrosine | (Tyr) | Glycine | (Gly) |

Each 3-letter codon represented in the table, e.g., AUG, CAU (otherwise known as a nucleotide triplet) corresponds to a trinucleotide of mRNA, having a 5'-end on the left and a 3'-end on the right. The letters stand for the purine or pyrimidine bases forming the nucleotide sequence. All DNA sequences given herein are those of the strand whose sequence corresponds to the mRNA sequence, with thymine (T) substituted for uracil (U).

In the following discussion reference will be made to the accompanying drawings in which.

The original source of genetic material was a library of human genomic clones. Screening of this library using pig relaxin cDNA probes yielded two clones containing coding sequences of human relaxin.

The mRNA sequence shown in FIGS. 2 and 3, was determined by the methods described hereinafter. It will be seen that a single intron of 3.4 kb interrupts the coding region of the connecting (C) peptide. The structure of human preprorelaxin was deduced from the genomic sequence by comparison with the homologous structures of pig and rat relaxin. Confirmation of the A and B peptide chain structures has been provided by synthesis and chain recombination in vitro which produces a material which is biologically active in the uterine contraction assay.

The mode of in vitro processing of the preprorelaxin is not yet fully known but by analogy with pig relaxin cleavage of the signal peptide would be expected to occur at the $Ala^{-1}$-$Lys^{1}$ bond. Similarly excision of the C peptide is predicted to occur at $Leu^{32}$ - $Ser^{33}$ and $Arg^{136}$ - $Arg^{137}$, thus giving the B and A chains of respectively 32 and 24 residues.

As noted in our studies on pig relaxin, there are core sequences in the pig relaxin B and A chains which contain all the essential elements for biological activity. Our synthetic studies on the human relaxin chain show similar results, as set out in more detail hereinafter.

According to one aspect of the present invention, there is provided a gene for the expression of human preprorelaxin.

Figure 2:
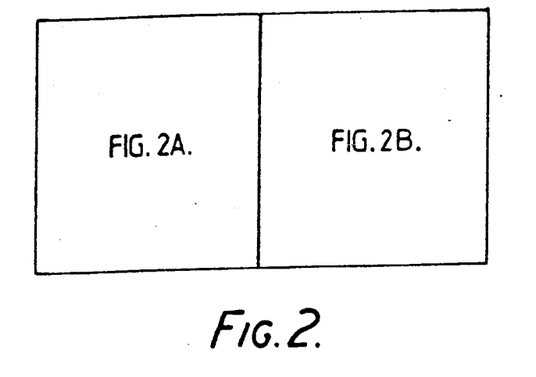
FIG. 2 shows the mRNA sequence of the coding region of the human relaxin gene and the amino-acid sequence of human preprorelaxin.
Figure 2A:
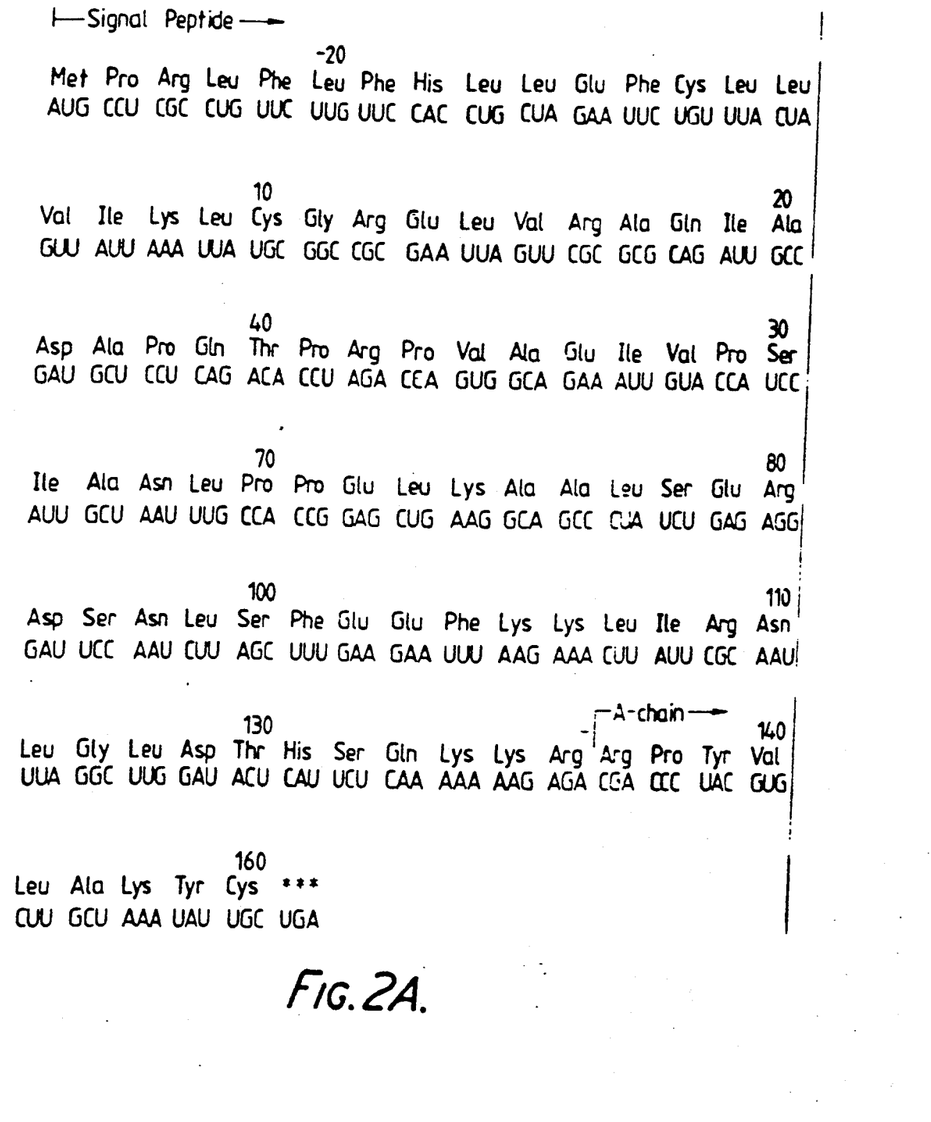
Figure 2B:
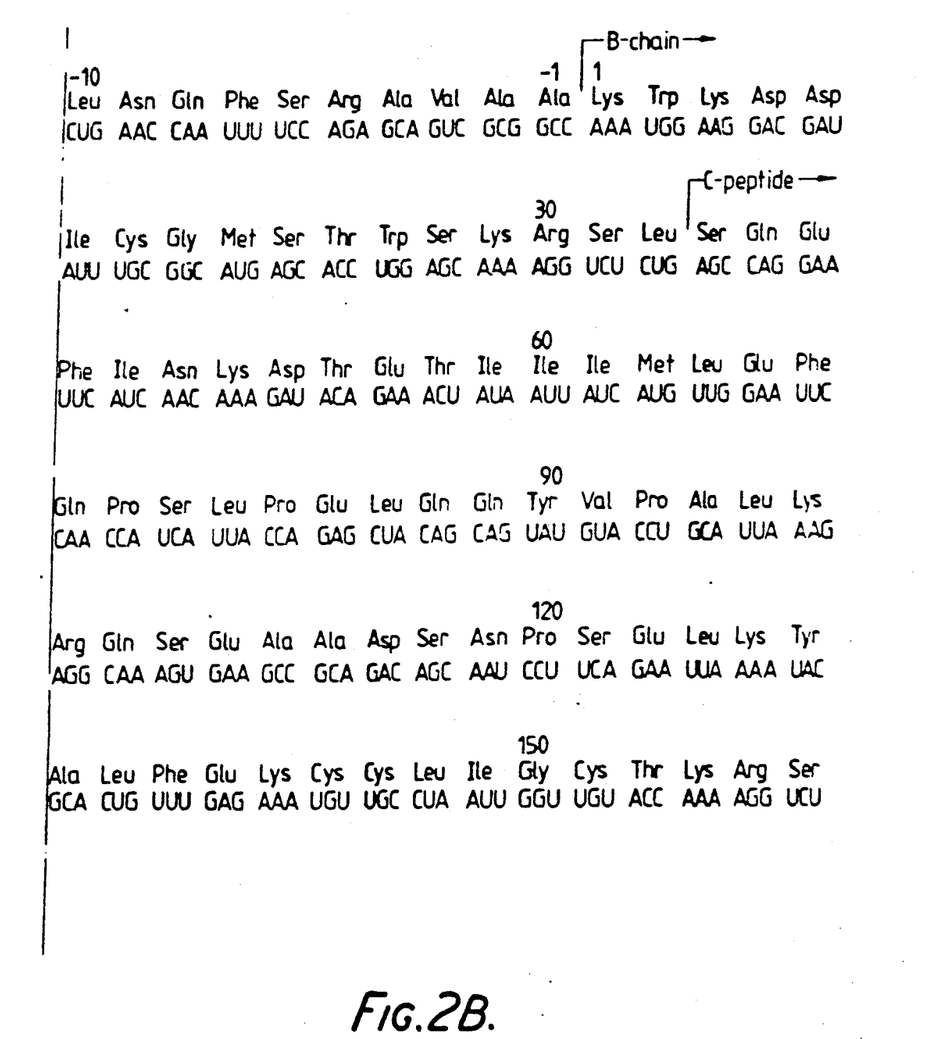

More specifically, this aspect of the invention provides a double-stranded DNA fragment for the expression of human preprorelaxin, which comprises a coding strand and a complementary strand corresponding to the complete mRNA (codons −25 to 160) sequence shown in FIG. 2 of the accompanying drawings.

The invention also includes any sub-unit of the preprorelaxin gene sequence described herein, or any equivalent of the said sequence or sub-unit. Among the sub-units to be included by this statement are genes which exclude non-coding regions, such as those shown in FIG. 3, genes containing the individual structural genes coding for the signal peptide chain and the A, B and C chains of human preprorelaxin (see FIG. 3) and any combinations of these chains, e.g., the genes for expressing the A and B peptide chains, separately or as prorelaxin (with the C chain).

Thus according to another aspect of the present invention, there is provided a gene for the expression of human prorelaxin.

More specifically, this aspect of the invention provides a double-stranded DNA fragment for the expression of human prorelaxin, which comprises a coding strand and a complementary strand corresponding to the codons numbered as 1 to 160 of the mRNA sequence shown in FIG. 2 of the accompanying drawings.

According to a further aspect of the present invention, there are provided genes for the separate expression of the A, B and C chains of human relaxin or any combination of two or more of the said chains.

More specifically, this aspect of the invention provides double-stranded DNA fragments for the separate expression of the A and/or B and/or C chains of human relaxin, which comprise a coding strand and a complementary strand corresponding to the codons numbered 1 to 32, 33 to 136 and 137 to 160 of the mRNA sequence shown in FIG. 2 of the accompanying drawings.

The genes described above in addition to the codons specified may also include the appropriate "start" and "stop" codons, i.e., AUG and UGA respectively (codons −26 and 161 in FIG. 2).

Those skilled in the art will appreciate that polymorphic forms of the genes may exist. Such forms are included in the present invention.

The invention further includes the complements of the above sequences, sub-units or equivalents, and the corresponding RNA sequences, sub-units or equivalents.

According to another aspect of the present invention there is provided a DNA transfer vector comprising the deoxynucleotide sequences corresponding to the genes defined above.

As shown above, the genetic code contains redundancies, that is certain amino acids are coded for by more than one codon. Thus the invention includes deoxynucleotide sequences in which the codons depicted in the drawings, or their cDNA equivalents are replaced by other codons which code for the same amino-acid.

Furthermore, as already indicated above, peptides with relaxin activity may be produced which differ from the B and/or A chain structures of natural relaxin. Such differences may involve deletion of one or more amino acids and/or addition of further amino acids and/or substitution of different amino acids in the natural chains.

Thus the invention also includes genes and DNA transfer vectors as described above wherein one or more of the natural codons are deleted and/or are replaced by codons which code for amino acids other than that coded by the natural codon, and/or further codons are added to the natural sequence.

The transfer vectors of the invention may also include inter alia, genetic information which ensures their replication when transferred to a host cell. Such cells may include, for example, the cells of prokaryotic microorganisms, such as bacteria, yeasts and moulds, and also eukaryotic cells, including mammalian cells and cell lines.

Examples of transfer vectors commonly used in bacterial genetics are plasmids and the DNA of certain bacteriophages. Both phage DNA and bacterial plasmids have been used as the transfer vectors in the present work. It will be understood however, that other types of transfer vectors may be employed. The general techniques of forming such transfer vectors and transforming them into microorganisms are well known in the art.

The invention also includes a prokaryotic or eukaryotic cell transformed by any of the transfer vectors described above.

One preferred microorganism is the very familiar *Escherichia coli*, but any other suitable microorganism may be used.

According to a still further aspect of the present invention, there is provided a process for making a DNA transfer vector for use in maintaining and replicating a deoxynucleotide sequence coding for human preprorelaxin, characterised by ligating a deoxynucleotide sequence coding for human preprorelaxin with a DNA molecule prepared by cleaving a transfer vector with a restriction enzyme.

DNA transfer vectors for use in maintaining and replicating deoxynucleotide sequences coding for human prorelaxin and for the A and B chains of human relaxin may be similarly prepared from the appropriate deoxynucleotides.

The A and B peptide chains, and also prorelaxin and preprorelaxin may be prepared by the usual process of gene expression, that is by growing cells containing the appropriate transformed transfer vector and isolating and purifying the required peptide(s) produced by the cells.

Thus, the invention further includes a process for making a fusion protein comprising the amino acid sequence of human preprorelaxin as its C-terminal sequence and a portion of a prokaryotic or eukaryotic protein as its N-terminal sequence, characterised by incubating a cell culture transformed by an expression transfer vector comprising a deoxynucleotide sequence coding for human preprorelaxin, prepared in accordance with the process described above.

Fusion proteins comprising the amino acid sequences for human prorelaxin and the A and B chains of human relaxin may be similarly prepared.

The fusion peptide products thus produced will be in the form of a fusion protein in which the desired peptide is linked with a portion of a prokaryotic or eukaryotic protein characteristic of the host cell. Such fusion proteins also form a part of this invention.

The invention also includes a process for synthesizing human prorelaxin comprising the A and B peptides separated from each other by a C peptide, characterised by incubating a culture of cells, transformed by an expression transfer vector comprising a deoxynucleotide sequence coding for said human prorelaxin, prepared as described above, under conditions suitable for expression of said sequence coding for human prorelaxin, and purifying human prorelaxin from the lysate or culture medium of said cells.

The peptide of interest can be recovered from the fusion product by any suitable known cleavage procedure.

As already indicated above the transfer vector may be modified by codon substitution /deletion/addition and such modifications will give rise to modified fusion peptides. In this way appropriate modifications may be made to facilitate the cleavage of the fusion peptides, for example, at the junction of B/C or C/A chains or to modify the peptide chain behaviour during subsequent chemical or biological processing.

As indicated above, the invention also provides human relaxin, prorelaxin and preprorelaxin.

Relaxin may be prepared by direct combination of the separate A and B chains by any of the procedures currently known and used for the preparation of insulin.

Also in a similar manner to insulin, relaxin may be prepared from prorelaxin by oxidizing or otherwise converting the sulfhydryl groups on the A and B peptides of relaxin, prepared as described herein, to form disulfide crosslinks between said A and B peptides, and then excising the C peptides, for example, by an enzyme-catalyzed hydrolysis specific for the bonds joining the C peptide to the A and B peptides.

Accordingly, the present invention further provides a method for the synthesis of human relaxin which comprises combining the A and B chains of relaxin (in their full-length, shortened or modified forms) by methods known per se for combination of A and B chains of human insulin.

One such method comprises reducing a mixture of the S-sulphonated A and B chains and then allowing the mixture to oxidize in air.

We have also found that the efficiency of the above procedure is improved when one or both of the A and B chains is in the form of an S-thioethyl-cys derivative rather than the S-sulpho form.

In our. Australian Patent Application No.15413/83 (PF 4385/82) we also showed that one or both of the A and B chains of relaxin can be shortened at the amino and/or carboxy terminii without significant loss of biological activity and with improved combination yields. These techniques apply equally to the preparation of human relaxin.

Another aspect of the invention provides a human relaxin analogue consisting essentially of shortened and/or modified forms of the natural B and/or A peptide chains.

This aspect of the invention also provides a method for producing a human relaxin analogue which comprises the step of forming the shortened and/or modified B and/or A peptide chains and combining them by any of the methods described above.

Our investigations with both pig and human relaxin show that relaxin activity may be present with A chains as short as A(10-24) and B chains as short as B(10-22) although the expected practical minima are respectively A(4-24) and B(4-23).

In general, the A chain can be varied from A(1-24) to A(10-24) and B chain from B(1-32) to B(10-22).

The preferred combinations are derived from:

| A | B |
|---|---|
| (1-24) | (1-23) |
| any of (2-24) | with any of (up to) |
| (3-24) | (1-32) |

Modifications of the B and/or A chains, in accordance with the present invention may involve either "genetic" modification, as described above or chemical modification of the B and/or A chains (in either full-length or shortened form) prior to combination by the method of the invention. Two types of modification may be employed, either singly or in combination.

The first type involves the modification of one or more of the amino-acids which occur in the natural or shortened B and/or A chains. Such modification will generally involve protection of active groups on one or more of the amino-acids by methods known per se, and the protecting groups may, if desired, be removed after combination of the (modified) A and B chains.

Examples of this type of modification include the acetylation, formylation or similar protection of free amino groups, including the N-terminal, amidation of C-terminal groups, or the formation of esters of hydroxyl or carboxylic groups. The formyl group is a typical example of a readily-removable protecting group.

The second type of modification includes replacement of one or more of the natural amino-acids in the B and/or A chains with a different amino acid (including the D-form of a natural amino-acid). This general type of modification may also involve the deletion of a natural amino-acid from the chain or the addition of one or more extra amino-acids to the chain.

The purpose of such modifications is to enhance the combination yields of the A and B chains, while maintaining the activity of the product, i.e., relaxin or an analogue thereof, or to enhance or modify the activity of the product for a given combination yield. Such modification may extend to the production of synthetic analogues which have relaxin-blocking or -antagonistic effects.

A specific example of the first type of modification is the modification of the tryptophan (Trp) residue at B2 by addition of a formyl group.

Examples of the second type of modification are replacement of the Met moiety at B24 with norleucine (Nle), valine (Val), alanine (Ala), glycine (Gly), serine (Ser) or homoserine (HomoSer).

The invention in this aspect also includes human relaxin analogues formed from natural or shortened B and/or A chains modified in accordance with the invention as described above.

The A and B peptide chains, and also prorelaxin and preprorelaxin may be prepared by the usual process of gene expression, that is by growing a microorganism containing the appropriate transformed transfer vector and isolating and purifying the required peptide(s) produced by the microorganism.

The peptide products thus produced may be in the form of a fusion protein in which, the desired peptide is linked with a portion of a prokaryotic protein The invention is further described and illustrated by the following description of the experimental procedures used and the results obtained thereby.

A. EXPERIMENTAL PROCEDURES

(i) Bacterial and Phage Strains $E.coli$ RR1 was used as the bacterial host for recombinant plasmids (pBR322) containing porcine relaxin cDNA. insertions as described previously (7).

The library of human genomic clones was kindly provided by T. Maniatis. Genomic DNA fragments of about 15-20 kb, from the partial Hae 111/Alu 1 fragmentation of the human DNA (9), were cloned by linkers into the lambda phase vector Charon 4A (10) and propagated in $E.coli$ LE392 cells.

Phage DNA (after clone selection) was prepared following lysis of $E.coli$ DP50supF cells in 1 liter cultures (10).

Small DNA fragments (from fragmentation of phage DNA) were subcloned for sequence analysis into the M13 bacteriophage vectors mp7.1, mp8 and mp9 (kindly provided by Dr. J. Messing) and transformed into $E.coli$ JM101 cells.

(ii) Preparation of Hybridization Probes (Porcine DNA)

Radiolabelled probes were prepared by primed synthesis on various DNA fragments using denatured random primers (3 or 4 bases) of calf thymus DNA (11). The porcine DNA template (100-200 ng) was denatured with the random primers (1 μg) by boiling in 20 μl of $H_2O$ for 2 minutes. Synthesis was initiated by the addition of a 30 μl reaction mixture containing 50 mM Tris-HCl pH 8.0, 50 mM NaCl, 1 mM DTT, 10 mM $MgCl_2$, 5 units of $E.coli$ DNA Polymerase 1,500 M each of dCTP, dGTP, dTTP and 0.3 μM α-[$^{32}$P]-dATP (approx. 3000 Ci/mmol, Amersham). After incubation at 37° for 30 minutes the reaction was terminated by dilution into 300 μl of a buffer containing 0.3M NaCl, 10 mM Tris-HCl, pH 8.0, 1 mM EDTA and passed through a Sephadex-G50 column, (1 cm×5 cm) in the same buffer. The radiolabelled probe was collected from the peak fractions at void volume and precipitated with 2 volumes of ethanol at −20° C. for 2 hours using tRNA (10 μg) as carrier.

(iii) Screening Procedures Lambda phage (λ) containing genomic DNA fragments were grown on soft agar at about $10^5$ phage/13 cm diam. plate and transferred to nitrocellulose filters (Schleicher & Schull BA85) as described by Benton and Davis (12). Filters were hybridized with the radiolabelled probe at 40° C. for 18 hours in modified Denhart's solution (13) containing 5×SSC and 25% formamide. Filters were washed in 2×SSC at 30° for 1 hour before exposing to x-ray film (Kodak XS-5) for 24 hours. Regions of the plate which exhibited positive hybridization were subcultured and rescreened successively until single positive plaques could be selected. Phage were harvested after lysis of 1 liter cultures of *E.coli* I DP50supF cells and DNA prepared by the methods described by Maniatis (10) and Yamamoto and Alberts (14).

(iv) DNA Sequence Analysis

Restriction fragments of the selected recombinant phage were subcloned directly into the Eco R1, Pst 1 or Sma 1 site of phage M13mp8. Ligations were carried out in 20 μl reactions containing 10 mM Tris-HCl pH 8.0, 10 mM $MgCl_2$, 1 mM DTT, 1 mM ATP, 1 unit of T4 DNA ligase, DNA (100 ng) and the M13 phage vector (50 ng). After incubation at 40° overnight recombinant DNA was transformed into *E.coli* JM101 cells (15). Plaques containing the coding region were selected by a similar technique as described for the genomic screens above, except the M13 phage were plated at lower density ($10^3$ phage/9 cm diam. plate). Positive plaques were grown for a preparative yield of either single stranded template or replicative double stranded (rf) form (15). Single stranded templates were sequenced directly by the method of Sanger et al (16) using either an M13-specific primer (Collaborative Research) or synthetic primers complementary to various sequences in the coding region. Complete sequence analysis of the subclones was obtained by cleavage of the rf form at several sites with various restriction enzymes followed by subcloning into M13 by blunt end ligation (15) or by directly end-labelling fragments and sequencing by the method of Maxam and Gilbert (17). DNA sequence was analysed and compared to the porcine and rat relaxin sequences using computer programmes (18).

B. RESULTS

In the following discussion, reference will be made to the drawings.

Figure 1:
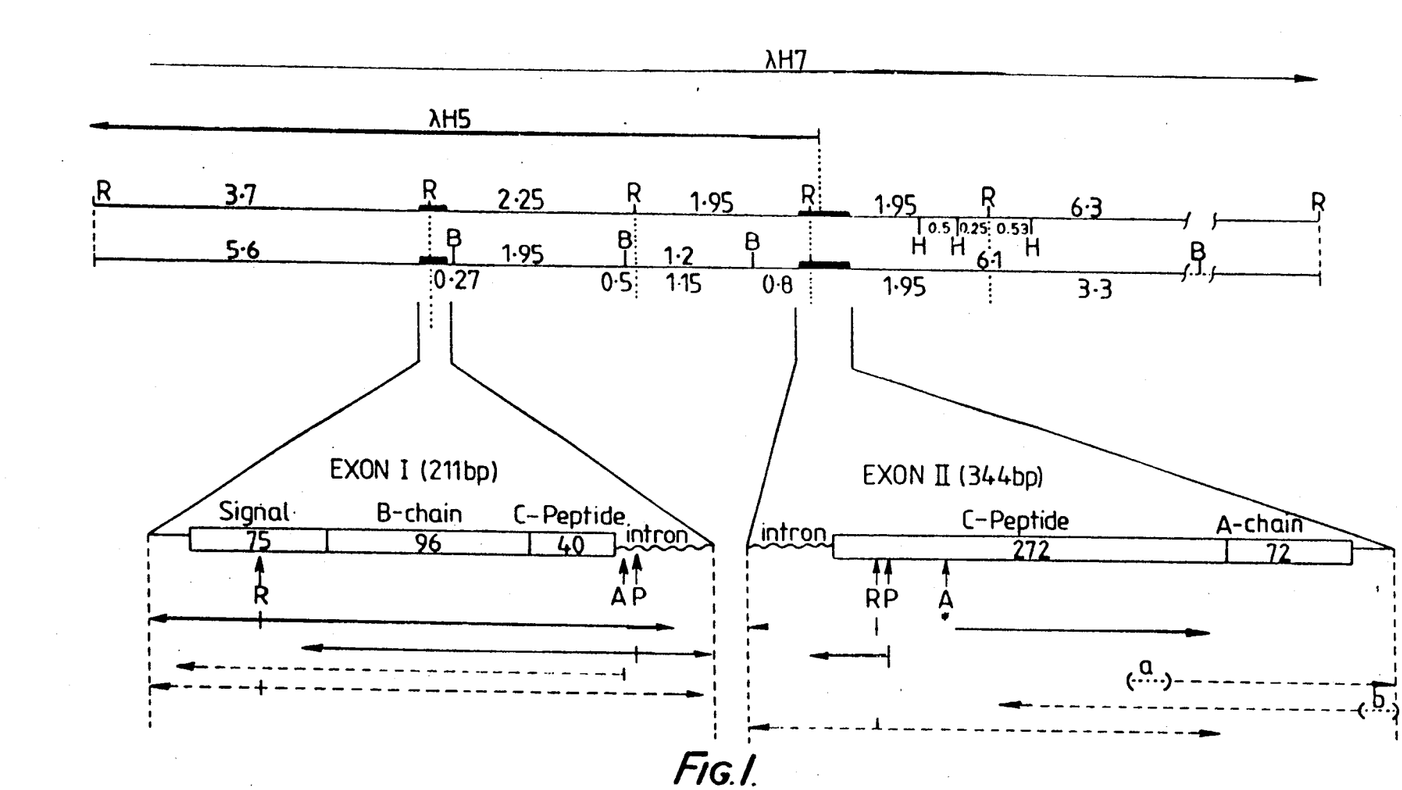
FIG. 1 is an abbreviated restriction enzyme map of the two genomic clones mentioned below.

FIG. 1 shows an abbreviated restriction enzyme map of the genomic clones.

Sizes are given in kilobase-pairs (kb) and cleavage sites are designated EcoR1 (R), Pst 1(P) and Hpa 11(H). The genomic clone λH5 terminates at an Eco R1 linker attached to the Alu 1 site in the C peptide (exon II) (A* in FIG. 1). The definitive nucleotide sequence over the coding region was compiled from the genomic clone λH7 by subcloning Eco R1 and Pst 1 fragments into M13mp8 and then either:

(1) direct sequencing shown by dashed lines in FIG. 1 (–) on M13 templates (2) direct sequencing using synthetic nucleotide primers shown by dotted lines (...)

(3) end-labelling DNA fragments and sequencing shown by solid lines (—) by chemical degradation.

The primers used for sequencing were a: 5′TTCGCAATAGGCA and b: 5′GCACAAT-TAGCT.

FIG. 2 shows the coding region of the human relaxin gene.

Figure 3:
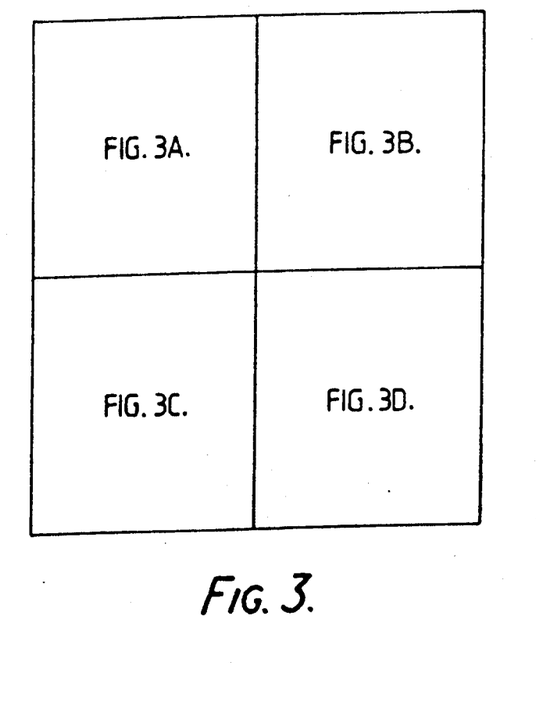
FIG. 3 shows a comparison of the human preprorelaxin and mRNA sequences with the corresponding sequences for porcine preprorelaxin.
Figure 3A:
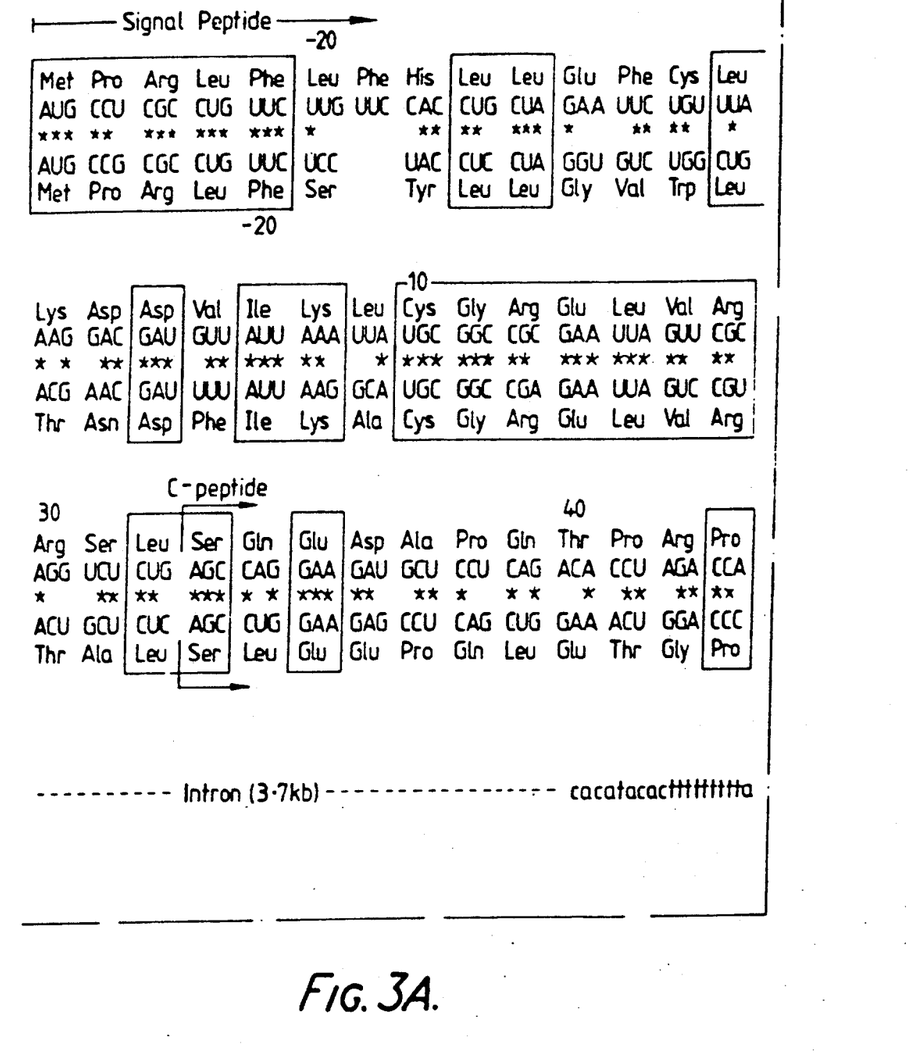
Figure 3B:
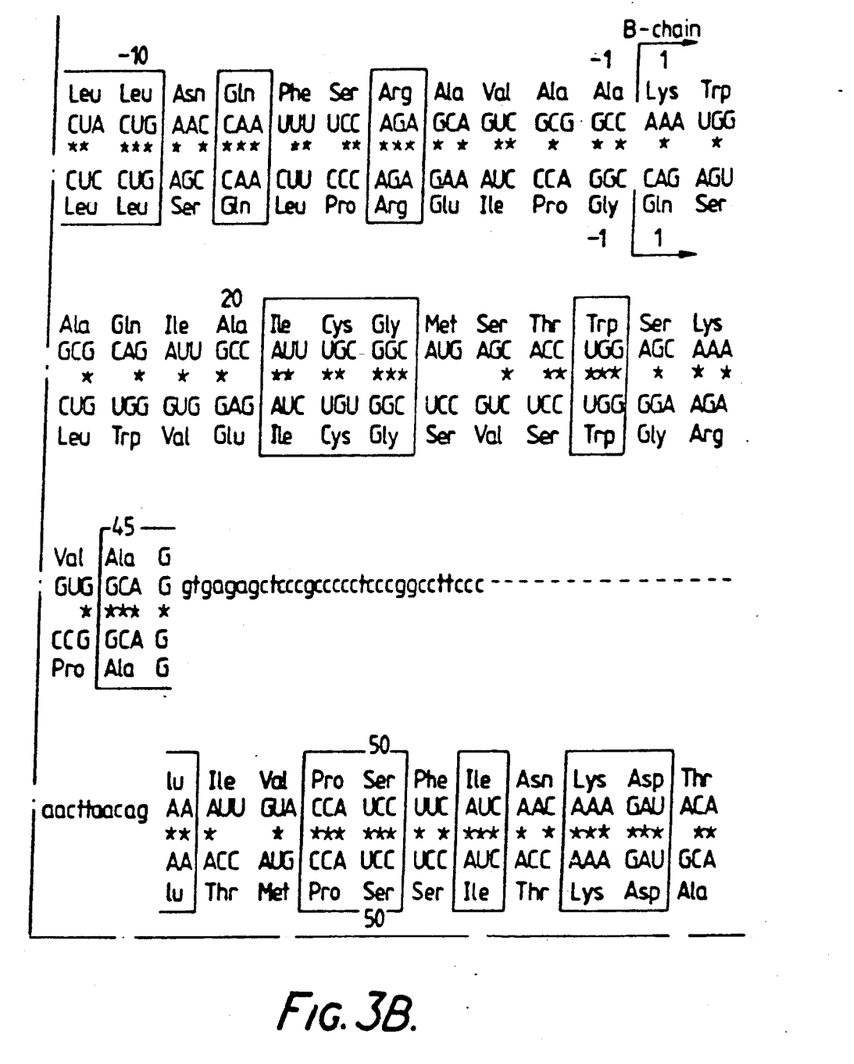
Figure 3C:
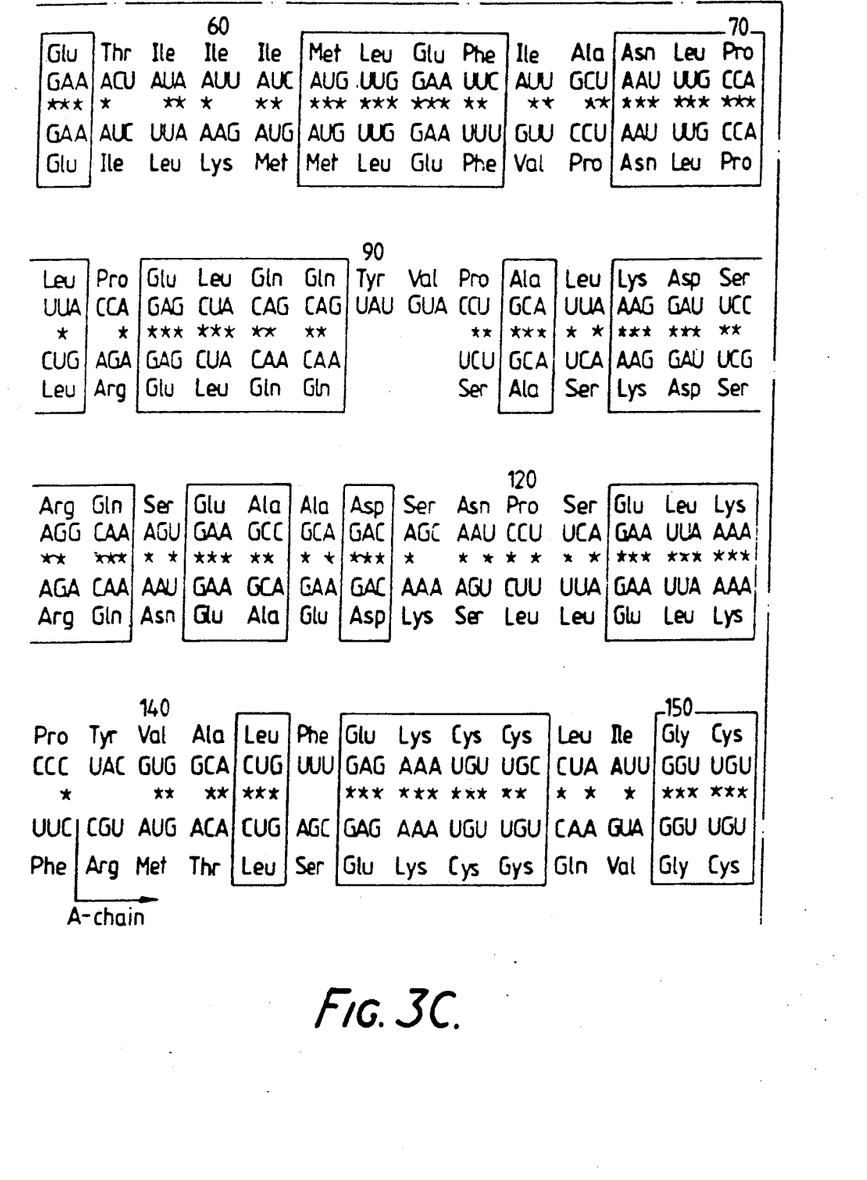
Figure 3D:
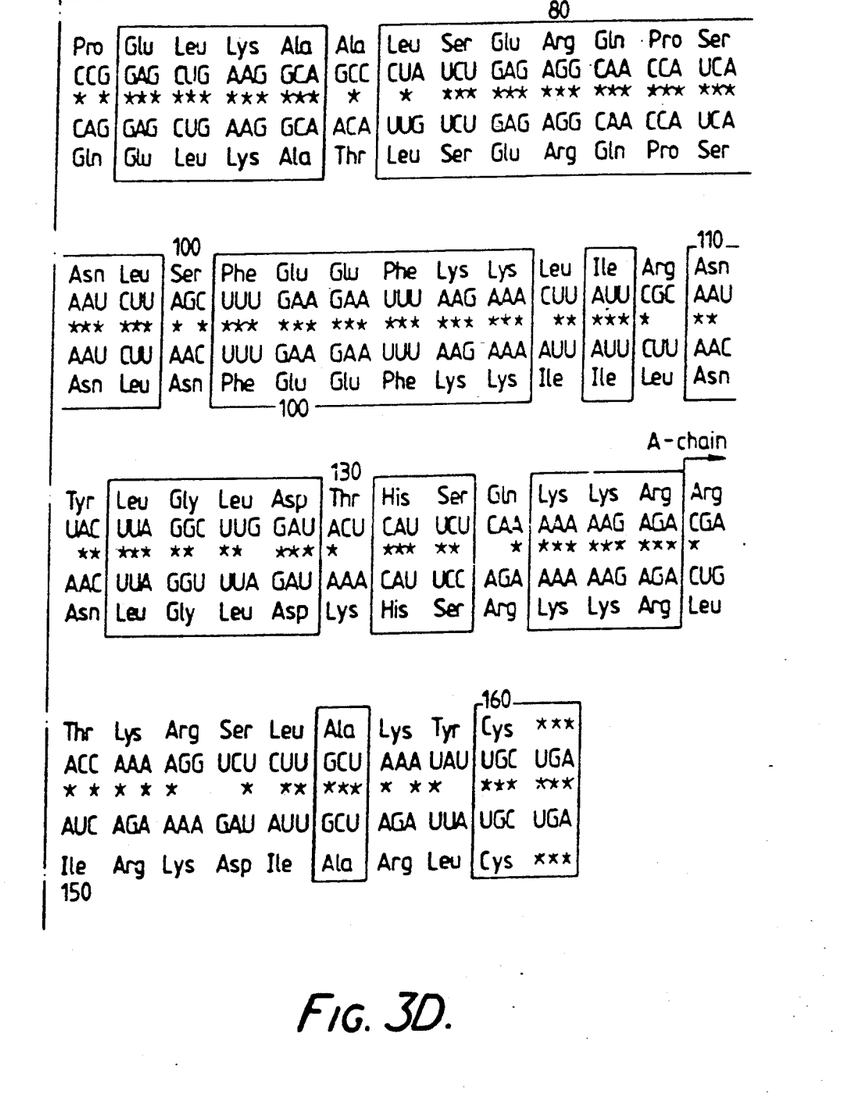

A comparison of the human preprorelaxin amino acid and mRNA sequence (upper) with the corresponding porcine relaxin sequence (lower) is shown in FIG. 3. The sequences have been aligned to maximize homology with nucleotide identities being indicated by asterisks and amino acid homologies by boxed-in areas. Amino acids are numbered from the start of the B-chain. The intron sequence at the exon/intron/exon boundaries is presented in lower case DNA notation.

(i) Isolation and Characterization of Genomic Clones

Human genomic clones were identified by screening the library with probes made from a short (150 bp) fragment of the porcine relaxin cDNA clone corresponding to amino acids 45-95 in the C-peptide (7) as set out in FIG. 3 of the accompanying drawings. This fragment was excised from the clone by digestion with Hpa II and Hinfl and corresponded to the region of maximum homology (71% at the nucleotide level) between rat and porcine relaxin sequences. From the genomic clone bank, two strongly positive phage designated λH5 and λH7 were isolated. These positive clones were further characterized by restriction enzyme analysis using as probes two separate fragments of porcine relaxin cDNA specific for the 5′ and 3′ exon regions respectively (hereinafter called "exon I" and "exon II"). The two fragments were generated by cleavage of the porcine relaxin cDNA clone at a single Hpa II site which corresponds (within a few bases) to an intron site in the homologous rat relaxin gene (6). Southern blot analysis of the λH5 and λH7 clones revealed that the coding region of the human relaxin gene is interrupted by a single intron of 3.4 kb (see FIG. 1).

(ii) Sequence Analysis of the Genomic Clones

The strategy used was to subclone complete restriction digests of λH5 and λH7 into M13 vectors and then screen using porcine relaxin probes specific for exons I and II. The positive subclones were sequenced by a combination of techniques described in the methods section (A(iv) above).

The exon II region of the λH7 clone was contained in a 2.0 kb EcoR1 fragment beginning at an Eco R1 site in the C-peptide and continuing through the entire coding sequence of the A chain to the termination codon (see FIG. 1). Sequencing of this fragment was aided considerably by the synthesis of nucleotide primers specific for regions around the A chain which were used to prime directly on the M13 template containing the entire 2.0 kb fragment. The subcloned Eco R1 fragment containing the remaining 53 bp of the C-peptide in exon II could not be identified with the porcine cDNA as a probe. The sequence over this region was obtained by a subcloned Pst 1 fragment from λH7 which contained the entire exon II region.

Sequencing the exon II region of λH5 revealed an extremely short 70 bp fragment beginning at the same Eco R1 site in the C-peptide as λH7 (see FIG. 1) but terminating with an Eco R1 linker which had been attached to an Alu 1 site in the original genomic DNA during the generation of the genomic library. Thus λH5 was designated an incomplete clone of the relaxin gene and was not analysed further.

Sequence analysis of the exon I region was slightly complicated by an Eco R1 site in the signal peptide which necessitated the independent sequencing of two Eco R1 fragment subclones. The overlap over the Eco R1 site was supported by the identification of a Alu I subclone from λH7 which contained the overlapping sequence.

C. Synthesis of a modified human relaxin (hRLX) A(1-24) - B(1-25)

(i) Synthesis of Human Relaxin A-chain, hRLX A(1-24)

The amino acid sequence corresponding to residues 1 to 24 of the human relaxin A-chain, deduced as described above from the nucleotide sequence of the genomic clone, was synthesized by the solid-phase procedure according to the general principles described by Merrifield (e.g. Barany, G. and Merrifield, R. B. In "The Peptides". Ed. E. Gross & J. Meienhofer, Academic Press, N.Y., pp. 1-284, 1980).

N-α-tertiarybutyloxycarbonyl*-4-methyl-benzyl-L-cysteine (*hereinafter "BOC") was coupled to a 1% crosslinked polystyrene resin via the phenylacetamido-methyl (PAM) linkage to a level of 0.30 mmole/gm using the method of Tam et al., (Synthesis 12, 955-957, 1979). The BOC-L-CYS-PAM resin (8.0 gm) was transferred to the reaction vessel of a Beckman Model 990 Peptide Synthesizer and the amino acid sequence from residues 23 through to 1 was assembled by the stepwise addition of each suitably protected amino acid. The amino terminal BOC protecting group of each amino acid was removed by treatment of the resin with 35% trifluoroacetic acid in methylene chloride for 30 minutes followed by neutralization with 5% diisopropylethylamine in methylene chloride for 15 minutes. After each treatment the resin was washed thoroughly with methylene chloride. The next amino acid in the sequence (suitably protected at the α-amino with the BOC group and where necessary with the side-chain functional group appropriately protected) was coupled to the resin using dicyclohexylcarbodiimide (DCC). The resin was stirred with the amino acid in methylene chloride for 10 minutes prior to the introduction of the DCC which was also dissolved in methylene chloride. A 2.5 molar excess (6.0 mmole) of amino acid and DCC was used for each coupling. After stirring for 1 hour a sample of the resin was removed from the reaction mixture and tested for the presence of free amino groups using the ninhydrin procedure of Kaiser et al. (Anal. Biochem., 34, 595-598, 1970). If the ninhydrin test was negative indicating complete coupling the reaction cycle was continued with BOC deprotection, neutralization and coupling of the next amino acid. For a positive ninhydrin test the coupling reaction was repeated with further amino acid and DCC.

Amino acids with side-chain functional groups were used as the following protected derivatives: N-α-BOC-2,6-dichlorobenzyl-L-tyrosine, N-α-BOC-ξ-chlorobenzyloxycarbonyl-L-lysine; N-α-BOC-L-serine O-benzyl ether; N-α-amyloxycarbonyl -$N^G$-tosyl-L-arginine; N-α-BOC-L-threonine O-benzyl ether; N-α-BOC-S-ethyl mercapto-L-cysteine (for CYS at a chain sequence position 15, 11 and 10); N-α-BOC-L-glutamic acid-γ-benzyl ester.

Following the assembly of the 1-24 peptide sequence, the final BOC group on the amino terminal arginine was removed using the deprotection neutralization cycle and the peptide-resin dried in vacuo (wt of peptide resin 17.0 gm). A portion of the peptide-resin (2 gm) was treated with anhydrous hydrogen fluoride in the presence of anisole (2 ml) at 0° C. for 30 minutes. The total time for contact of the resin-peptide with hydrogen fluoride (HF) was kept to a minimum (not more than 70 minutes) by rapid removal of the HF under oil-pump vacuum. The resin-peptide was then washed several times with ethyl acetate to remove excess anisole, the peptide extracted into 1M acetic acid and the solution lyophilized. The yield of crude peptide, (with the cysteines at positions 10, 11 and 15 still protected as the S-thioethyl derivative) was 440 mg. Initial purification of the crude peptide was by gel-filtration on Biogel P10 in 0.1M acetic acid. The fractions representing the major peak from this column, which eluted at a position corresponding to a molecular weight of approximately 3000, were collected and lyophilized. Amino acid analysis of a sample of this peptide indicated that all the amino acids of the 1-24 sequence were present in the correct ratio.

Further purification of the [S-thioethyl $Cys^{10,11,15}$]-hRLX A(1-24) peptide was effected by preparative reverse-phase HPLC on a Waters C-18 Bondapak column using a 0.1% TFA-water/acetonitrile solvent system.

A sample (160 mg) of the peptide purified by gel-filtration was S-sulfonated with a mixture of sodium sulfite and sodium tetrathionate (total reaction time of 3 hours) according to the method described by Du et al., (Scientia Sinica, 10I, 84-104 (1961)). The precipitate which formed during the S-sulfonation reaction was removed by filtration and both the precipitate and the supernatant solution dialyzed against distilled water at 4° C. for 48 hours. The contents of the dialysis bags were lyophilized to yield 81.4 mg of peptide from the supernatant solution and 53.2 mg of peptide from the precipitate which occurred during the S-sulfonation reaction. A sample of the 'soluble' [S-sulfo $Cys^{10,11,15,24}$] hRLX A(1-24) peptide was purified by ion exchange chromatography on DEAE-cellulose in tris-HCl buffer pH 8.3. Peptide was eluted from the column with a linear gradient of NaCl in tris-HCl buffer using a conductivity range of 3.0 mS to 85.0 mS. Fractions representing the major peak eluting from the ion-exchange column at conductivity 20 to 30 mS were dialyzed and the peptide recovered by lyophilization. Prepared HPLC was used to further purify the S-sulfonated peptide.

(ii) Synthesis of Shortened Human Relaxin B-chain, hRLX B(1-25)

The amino acid sequence corresponding to residues 1 to 25 of the human relaxin B-chain was synthesized using the procedures described above and commencing with 7.0 gm N-α-tertiarybutyloxycarbonyl-O-benzyl-L-serine-phenylacetamido-methyl polystyrene resin with a loading of 0.1 mmole Ser per gm. The side-chain protecting groups used in the A-chain synthesis were also employed for the B-chain including the S-ethyl derivative for both cysteines at positions 10 and 22. The aspartic acid residues at positions 4 and 5 were added as the N-α-BOC-ξ-benzyl ester derivative. The glutamine at position 18 was coupled by the active ester procedure using N-α-BOC-L-glutamine-p-nitrophenyl ester in DMF. Following coupling of the tryptophan at position 2, 0.1% indole was added to the trifluoroacetic acid deprotecting reagent and to the subsequent methylene chloride washes.

The final weight of peptide-resin after removal of the BOC group from the amino terminal lysine residue and vacuum-drying was 12.2 gm. A portion of the peptide resin (5 gm) was treated with anhydrous hydrogen fluoride in the presence of anisole (2 ml) at 0° C. for 30 minutes and the B-chain peptide isolated using the procedure described above for the A-chain. The crude [S-thioethyl $Cys^{10,22}$] hRLX B(1-25) (1.40 gm) was purified by gel filtration on BioGel P10 in 0.1 M acetic acid followed by preparative HPLC.

A sample (150 mg) of the peptide purified by gel filtration was S-sulfonated at pH 8.3 for 3 hours, the reaction mixture filtered and the precipitate and supernatant solutions dialyzed against distilled water. The 'soluble' peptide recovered after lyophilization was 92 mg; the 'insoluble' peptide was 55 mg. The S-sulfonated B-chain peptides were further purified by preparative HPLC using a C-18 reverse-phase column and 0.1% TFA-water-acetonitrile solvent system.

(iii) Chain Combination

The synthetic hRLX A(1-24) and hRLX B(1-25) peptides were combined using the procedure described by Chance and Hoffmann (Australian Patent Application No. 68844/81) for insulin chains wherein the S-sulfonated peptides were mixed in a ratio of A:B of 2:1 at a peptide concentration of 10 mg/ml in glycine buffer pH 10.5. Dithiothreitol in glycine buffer was then added in an amount to give a total of 1.0 sulfhydryl groups for each S-sulfo group. The reaction mixture was then stirred in an open vessel for 24 hours.

As a further modification to this procedure we have found that the chain combination reaction to form biologically active relaxin proceeded efficiently when one or preferably both of the peptide chains are used as their S-thioethyl-Cys derivatives rather than in the S-sulfo form specified by Chance and Hoffmann (op.cit.) in the case of insulin. The use of S-thioethyl Cys peptides eliminates a reaction and purification step required to convert the peptides to the S-sulfo derivatives. In our experience the S-sulfonation reaction of relaxin peptides is accompanied by side reactions which render the S-sulfo peptides difficult to purify resulting in low yields.

Using, the above conditions chain combination yields from 0.24 to 3.1% have been achieved as measured by biological activity in the rat uterine contractility assay of Wiqvist & Paul (Acta Endocrinol., 29, 135-136, 1958).

Example of Chain Combination Reaction

Human relaxin [S-thioethyl $Cys^{10,11,15}$] A(1-24) (3.60 mg dry wt., 2.0 mg peptide by amino acid analysis, 0.68 µmole) was dissolved in 200 µl of 0.1 M glycine buffer pH 10.5 in a 3 ml stoppered plastic centrifuge tube. Human relaxin [S-sulfo $Cys^{10,11}$] B(1-25) (1.89 mg, 1.0 mg peptide by amino acid analysis, 0.33 µmole) dissolved in 100 µl of 0.1 M glycine buffer pH 10.5 was added and the mixture agitated. An aliquot (15.2 µl, 1.73 µmole DTT) of a stock solution of dithithreitol (DTT) made up in 0.1 M glycine buffer pH 10.5 (1.15 µmole DTT in 10 ml) was added to the peptide solution and following a brief agitation the reaction mixture was allowed to stand at 4° C. for 24 hours open to the air. The mixture was then centrifuged and aliquot of the supernatant solution tested for relaxin biological activity in the rat uterine contractility assay. Aliquots of the reaction mixture inhibited the spontaneous contractions of the rat uterus in a dose-related manner. A 75 µl aliquot completely inhibited uterine contractions equivalent to a chain combination yield of 0.70% as compared to a native pig relaxin A22 B31 standard.

Additional Synthetic Human Relaxin Peptides Based Upon the H1-gene Sequence

The synthetic relaxin peptides listed in the following Table were prepared from the amino acid sequences for the A and B chains derived from the H1 human relaxin gene sequence shown in FIG. 2. The separate peptide chains were prepared and purified according to the procedure described above for the A(1-24) and B(1-25) peptides. A modification of these procedures was used for the B(3-25)amide and B(1-25)amide peptides, wherein the PAM resin linkage was replaced by the benzhydrylamine (BHA) polystyrene resin. Use of the BHA resin results in the formation of peptides with the C-terminus in the amide rather than free carboxy form.

Unless otherwise stated the chain combination reaction was performed as described previously with the A-chain as the S-thio ethyl Cys derivative and the B-chain as the S-sulfo Cys derivative.

All of the synthetic analogues in the following table exhibited relaxin-like biological activity in the rat uterine contractility assay. The combination yields of the separate peptide chains were calculated from the bioassay results using native pig relaxin A(1-22)-(1-31) as standard.

| Synthetic H1 human relaxin analogue | Combination Yield (based on B-chain amount) |
| --- | --- |
| A(1-24) + B(1-23) | 0.24% |
| A(1-24) + B(1-25) | 0.70% |
| A(1-24) + [$Ala^{24}$]B(1-26) | 0.92% |
| A(1-24) + B(1-32) | 2.00% |
| A(1-24) + B(1-25)amide | 0.80% |
| A(1-24) + B(1-25)amide with both chains in S-thioethyl form for chain combination reaction | 3.10% |
| A(1-24) + B(3-25)amide | 0.68% |
| A(1-24) + [N-formyl $TRP^2$]B(2-25) | 0.43% |

REFERENCES

1. Hisaw, F. L. Proc. Soc. Exp. Biol. Med. 23, 661-663 (1926).
2. Schwabe, C., McDonald, J. K. and Steinetz, B. C. Biochem. Biophys. Res. Commun. 75, 503-510 (1977).
3. James, R., Niall, H., Kwok, S. and Bryant-Greenwood, G. Nature, 267, 544-546 (1977).
4. John, M. J., Walsh, J. R., Borjesson, B. W. and Niall, H. D. Endocrinology 108, 726-729 (1981).
5. Schwabe, C., Gowan, L. K. and Reinig, J. W., Ann. N.Y. Acad. Sci. 380, 6-12 (1982).
6. Hudson, P., Haley, J., Cronk, M., Shine, J. and Niall, H. Nature, 291, 127-131 (1981).
7. Haley, J., Hudson, P., Scanlon, D., John, M., Cronk, M., Shine, J., Tregear, G. and Niall, H. DNA 1, 155-162 (1982).
8 Dayhoff, M. O., Schwartz, R. M., Chen, H. R., Hunt, L. T., Barker, W. C. and Orcutt, B. C. DNA 1, 51-58 (1981).
9. Lawn, R. M., Fritsch, E. F., Parker, R. C. Blake, G. and Maniatis, T. Cell, 15, 1157-1174 (1978).
10. Maniatis, T., Hardison, R. E., Lacy, E., Lauer, J., O'Connell, C., and Quon, D. Cell 15, 687-701 (1978).

11. Taylor, J. M., Illmersee, R., and Summers, J. Biochim. Biophys. Acta 442, 324-330 (1976),
12. Benton, W. D. and Davis, R. Science 196, 180-183 (1977).
13. Denhardt, D. T. Biochem. Biophys. Res. Commun. 23, 641-646 (1966).
14. Yamamoto, K. R. and Alberts, B. M. Virology 40, 734-744 (1970).
15. Sanger, F., Coulson, A. R., Barrell, B. G., Smith, A. J. A. and Roe, B. A. J. Mol. Biol. 143, 161-178 (1980).
16. Sanger, F., Nicklen, S. and Coulson, A. R. Proc. Natn. Acad. Sci. 74, 5463-5467 (1977).
17. Maxam, A. M. and Gilbert, W. Proc. Natn. Acad. Sci. 74, 560-564 (1977).
18. Staden, R. Nucl. Acids, Res. 6, 2601-2610 (1979).

We claim:

1. Essentially pure human H1-preprorelaxin, which is free of other human proteins.
2. Essentially pure human H1-prorelaxin, which is free of other human proteins.
3. The essentially pure human H1-prorelaxin as claimed in claim 2, comprising:
    (i) a human H1-relaxin A chain having the sequence:

```
        1              5              10
    Arg Pro Tyr Val Ala Leu Phe Glu Lys Cys Cys Leu
        15             20           24
    Ile Gly Cys Thr Lys Arg Ser Leu Ala Lys Tyr Cys;
```
    (ii) a human H1-relaxin B chain having the sequence:

```
        1              5              10
    Lys Trp Lys Asp Asp Val Ile Lys Leu Cys Gly Arg
        15             20
    Glu Leu Val Arg Ala Gln Ile Ala Ile Cys Gly Met
        25             30        32
    Ser Thr Trp Ser Lys Arg Ser Leu; and
```

(iii) a human H1-prorelaxin C chain having the amino acid sequence set forth in FIGS. 2A through 2D as arrayed in FIG. 2.
4. An essentially pure polypeptide, wherein said polypeptide comprises:
    (i) a human H1-relaxin A chain selected from the group consisting of A(1-24) to A(5-24), wherein amino acids 1-24 have the following sequence:

```
        1              5              10
    Arg Pro Tyr Val Ala Leu Phe Glu Lys Cys Cys Leu
        15             20           24
    Ile Gly Cys Thr Lys Arg Ser Leu Ala Lys Tyr Cys;
```
    (ii) a human H1-relaxin B chain selected from the group consisting of B(1-32) to B(4-23), wherein amino acids 1-32 have the following sequence:

```
        1              5              10
    Lys Trp Lys Asp Asp Val Ile Lys Leu Cys Gly Arg
        15             20
    Glu Leu Val Arg Ala Gln Ile Ala Ile Cys Gly Met
        25             30        32
    Ser Thr Trp Ser Lys Arg Ser Leu; and
```

(iii) a human H1-prorelaxin C chain having the amino acid sequence as set forth in FIGS. 2A through 2D as arranged in FIG. 2, wherein the C chain amino acid sequence is modified at the junction of the B/C and C/A chains to facilitate cleavage at the B/C and C/A junctions and subsequent excision of the C chain.
5. The essentially pure polypeptide according to claim 4, wherein the A and B chains of said polypeptide comprise:
    (i) a human H1-relaxin A chain selected from the group consisting of A(1-24) to A(3-24); and
    (ii) a human H1-relaxin B chain selected from the group consisting of B(1-32) to B(1-23).
6. The essentially pure polypeptide according to claim 4, wherein said B chain has been modified by replacement of the Met residue at B(24) with a member selected from the group consisting of valine, alanine, glycine and serine.
7. An essentially pure polypeptide selected from the group consisting of the signal, A, B and C polypeptide chains of human H1-preprorelaxin, which is free of other human proteins.
8. The essentially pure polypeptide as claimed in claim 7, wherein said A polypeptide chain is
    (i) a human H1-relaxin A chain selected from the group consisting of A(1-24) to A(5-24), wherein amino acids 1-24 have the following sequence:

```
        1              5              10
    Arg Pro Tyr Val Ala Leu Phe Glu Lys Cys Cys Leu
        15             20           24
    Ile Gly Cys Thr Lys Arg Ser Leu Ala Lys Tyr Cys
``` and, wherein said B polypeptide chain is
    (ii) a human H1-relaxin B chain selected from the group consisting of B(1-32) to B(4-23), wherein amino acids 1-32 have the following sequence:

```
        1              5              10
    Lys Trp Lys Asp Asp Val Ile Lys Leu Cys Gly Arg
        15             20
    Glu Leu Val Arg Ala Gln Ile Ala Ile Cys Gly Met
        25             30        32
    Ser Thr Trp Ser Lys Arg Ser Leu,
``` and, wherein said C polypeptide chain is
    (iii) a human H1-prorelaxin C chain having the amino acid sequence as set forth in FIGS. 2A through 2D as arranged in FIG. 2.
9. The essentially pure polypeptide as claimed in claim 8, wherein said A polypeptide chain is
    (i) a human H1-relaxin A chain selected from the group consisting of A(1-24) to A(3-24);
    and wherein said B polypeptide chain is
    (ii) a human H1-relaxin B chain selected from the group consisting of B(1-32) to B(1-23).
10. The essentially pure polypeptide as claimed in claim 8, wherein said B chain has been modified by one or more procedures selected from the group consisting of:
    (a) formylation of the Trp residue(s) at B(2), B(27) or both B(2) and B(27); and
    (b) replacement of the Met residue at B(24) with a member selected from the group consisting of norleucine, valine, alanine, glycine, serine and homoserine.

* * * * *